United States Patent [19]
Nakamura et al.

[11] Patent Number: 5,669,554
[45] Date of Patent: Sep. 23, 1997

[54] HUMIDITY CONTROL THERMAL ANALYZER

[75] Inventors: Nobutaka Nakamura; Ryoichi Kinoshita, both of Chiba, Japan

[73] Assignee: Seiko Instruments, Inc., Tokyo, Japan

[21] Appl. No.: 561,194

[22] Filed: Nov. 21, 1995

[30] Foreign Application Priority Data

Nov. 21, 1994 [JP] Japan .................... 6-286961

[51] Int. Cl.⁶ .................... G01N 25/00; B01F 3/02
[52] U.S. Cl. .................... 236/44 C; 165/222; 219/401; 374/14
[58] Field of Search .................... 236/44 C; 165/222; 374/14, 11, 10; 219/401

[56] References Cited

U.S. PATENT DOCUMENTS

| | | | |
|---|---|---|---|
| 3,110,442 | 11/1963 | Taylor | 236/44 C |
| 3,292,417 | 12/1966 | Hayden et al. | 374/14 |
| 3,825,723 | 7/1974 | Roeser | 236/44 C |

*Primary Examiner*—William E. Wayner
*Attorney, Agent, or Firm*—Loeb & Loeb LLP

[57] ABSTRACT

The humidity of the atmosphere contacting a sample and the water vapor partial pressure are program controlled and measured in a device having: a sample chamber which is provided with an inlet and an outlet for water vapor and which is capable of controlling a feedback temperature along with the sample stored therein; a warm water chamber for generating saturated water vapor pressure which has a gas inlet and an outlet connected to a pipe and which is capable of controlling the feedback temperature; a humidity program function generator for outputting a target humidity value for the sample chamber for each input time interval; a memory for storing a temperature-saturated water vapor pressure curve; and a calculator for calculating a control target temperature for the warm water chamber for generating the saturated water vapor pressure on the basis of the sample chamber target temperature output from a temperature program function generator, sample chamber target humidity of the sample chamber output from the humidity program function generator and the temperature-saturated water vapor pressure curve.

15 Claims, 3 Drawing Sheets

HUMIDITY CONTROL THERMAL ANALYZER

BACKGROUND OF THE INVENTION

The present invention relates to a new improved thermal analyzer device in which a signal representing a change in physical and chemical characteristics of a sample is measured as a function of temperature or time, wherein the humidity, or moisture content, of the periphery of the sample and the water vapor partial pressure of the atmosphere surrounding the sample can be program controlled and measured.

Thermal analysis is an effective means for investigating how the physical characteristics of a material change with temperature. Examples of thermal analyzers include differential scanning calorimeters (DSCs), differential thermal analyzers (DTAs), thermal gravimetric analyzers (TGs) and thermomechanical analyzers (TMAs). These thermal analyzers are intended to measure the temperature dependency of various quantities, such as entropy convergence of a sample, differential temperature (qualitative entropy convergence), weight and length, respectively.

Further, the quality of the sample often changes under the influence of the atmosphere around the sample. Consequently, a thermal analyzer is generally used which adopts a mechanism for keeping atmospheric conditions at a definite level. For example, a structure may be provided in which the sample region is sealed to allow a gas exchange.

Further, with respect to the improvement of an analyzer for keeping at a constant level the temperature and the atmospheric humidity of a sample region with respect to the aforementioned thermal analyzer, products is available on the market in the form of vapor generating attachments made by various manufacturers.

In the aforementioned prior art, it was impossible to scan the temperature in accordance with a program while keeping the relative humidity at a constant level, or to scan the temperature and the humidity at the same time. In other words, the humidity control at the time of temperature scanning was largely limited.

On the other hand, a problem arises in that the length of sample materials is largely affected by the temperature and humidity (existence of water) when an attempt is made to measure the thermal expansion and elasticity of polymer materials such as cellophane, nylon or the like. In other words, it is necessary to conduct experiments with consideration of the fact that the physical characteristics of materials are changed along with the plasticization of the material by humidity. In such a case, it is impossible to judge whether the observed change depends on temperature or on humidity unless the humidity is controlled in some manner while scanning, or varying, the temperature.

Further, when conducting studies of physical characteristics changes in hair after shampooing, an evaluation of the humidity dependency is indispensable. Consequently, it is required to measure the humidity dependency while actively varying the humidity. The aforementioned prior art does not sufficiently meet the these demands.

SUMMARY OF THE INVENTION

It is an object of the present invention to solve the aforementioned problems in an effective manner.

The above and other objects are achieved, according to the present invention, by a humidity control thermal analyzer comprising: a humidity control thermal analyzer comprising: a detector for detecting and measuring a physical characteristic of a sample; a sample chamber for housing the sample and which is provided with a vapor inlet and a vapor outlet for water vapor and which is capable of controlling the temperature of the sample housed in the sample chamber; a heat insulating pipe with heating means for preventing dew condensation, the pipe being connected to the vapor inlet of the sample chamber; a warm water container for generating water vapor, the container having a gas inlet and having a gas outlet which is connected to the pipe and which is capable of controlling the temperature of water in the container; a temperature program function generator for outputting a target temperature value of the sample chamber as a function of time; a humidity program function generator for outputting a target humidity value of the sample chamber as a function of time; a memory means for storing a temperature-saturated water vapor pressure curve; and a calculator connected to the function generators and the memory means for calculating a control target temperature for the water in the container for generating a saturated water vapor pressure on the basis of the sample chamber target temperature output from the temperature program function generator, the sample chamber target humidity value of the sample chamber output from the humidity program function generator and the temperature-saturated water vapor pressure curve, wherein the temperature of the sample and the humidity of the atmosphere contacting the sample are program controlled.

Objects according to the invention are further achieved by a humidity control thermal analyzer comprising: a detector for detecting and measuring a physical characteristic of a sample; a sample chamber for housing the sample and which is provided with a vapor inlet and a vapor outlet for water vapor and which is capable of controlling the temperature of the sample housed in the sample chamber; a sample temperature detector which is disposed in the sample chamber for detecting the temperature of the sample; a heat insulating pipe with heating means for preventing dew condensation, the pipe being connected to the vapor inlet of the sample chamber; a warm water container for generating water vapor, the container having a gas inlet and having a gas outlet which is connected to the pipe and which is capable of controlling the temperature of water in the container; a temperature program function generator for outputting a target temperature value of the sample chamber as a function of time; a humidity program function generator for outputting a target humidity value of the sample chamber as a function of time; a memory means for storing a temperature-saturated water vapor pressure curve; and a calculator connected to the sample temperature detector, the humidity program function generator and the memory means for calculating a control target temperature for the water in the container for generating a saturated water vapor pressure on the basis of the sample temperature detected by the sample temperature detector, the sample chamber target humidity value of the sample chamber output from the humidity program function generator and the temperature-saturated water vapor pressure curve, wherein the temperature of the sample and the humidity of the atmosphere contacting the sample are program controlled.

The function of the above-described thermal analyzer is as follows. When physical characteristics of the sample are measured as a function of both temperature and the humidity in accordance with the predetermined temperature program and predetermined humidity program by placing the sample in the sample chamber, the temperature of the sample chamber is fed back in accordance with the temperature program. At this time, to realize a vapor pressure value and a relative humidity value designated by the humidity program, the following calculation is performed immediately by the calculator on the basis of the relation between the temperature and the saturated water vapor pressure.

That is, when the humidity program is input at a vapor pressure value, this vapor pressure value is set as the vapor pressure value that should be generated in the warm water chamber for generating saturated water vapor pressure. Further, when the humidity program is input at a relative humidity value, the saturated vapor pressure which corresponds to the program temperature in the sample chamber is determined. By multiplying the saturated vapor pressure by the relative humidity value, a water vapor pressure that should be generated in the warm water chamber for generating saturated water vapor pressure can be obtained. The temperature corresponding to the vapor pressure thus obtained that should be generated in the warm water chamber for generating saturated water vapor pressure is determined as a control target temperature of the warm water chamber for generating saturated water vapor pressure.

Further, the temperature in the warm water chamber for generating saturated water vapor pressure is controlled in accordance with a control target temperature obtained by the calculator while the saturated water vapor which corresponds to the warm water temperature which is generated in the warm water chamber for generating saturated water vapor pressure is sent to a sample chamber via a heat insulating pipe with a heater provided with a dew condensation preventing means. At this time, the water vapor pressure in the sample chamber is given as a ratio of saturated water vapor pressure which corresponds to the temperature of the warm water chamber, and the relative humidity of the sample chamber is given as a ratio of saturated water vapor pressure which corresponds to the temperatures of the sample chamber and the warm water chamber. Consequently, the relative humidity agrees with the indication value of the humidity program and the temperature in the sample chamber and the humidity are simultaneously controlled in accordance with the program, thereby attaining the object of measuring the physical characteristics as a function of the temperature and the humidity.

DESCRIPTION OF THE PREFERRED EMBODIMENTS

Figure 1:
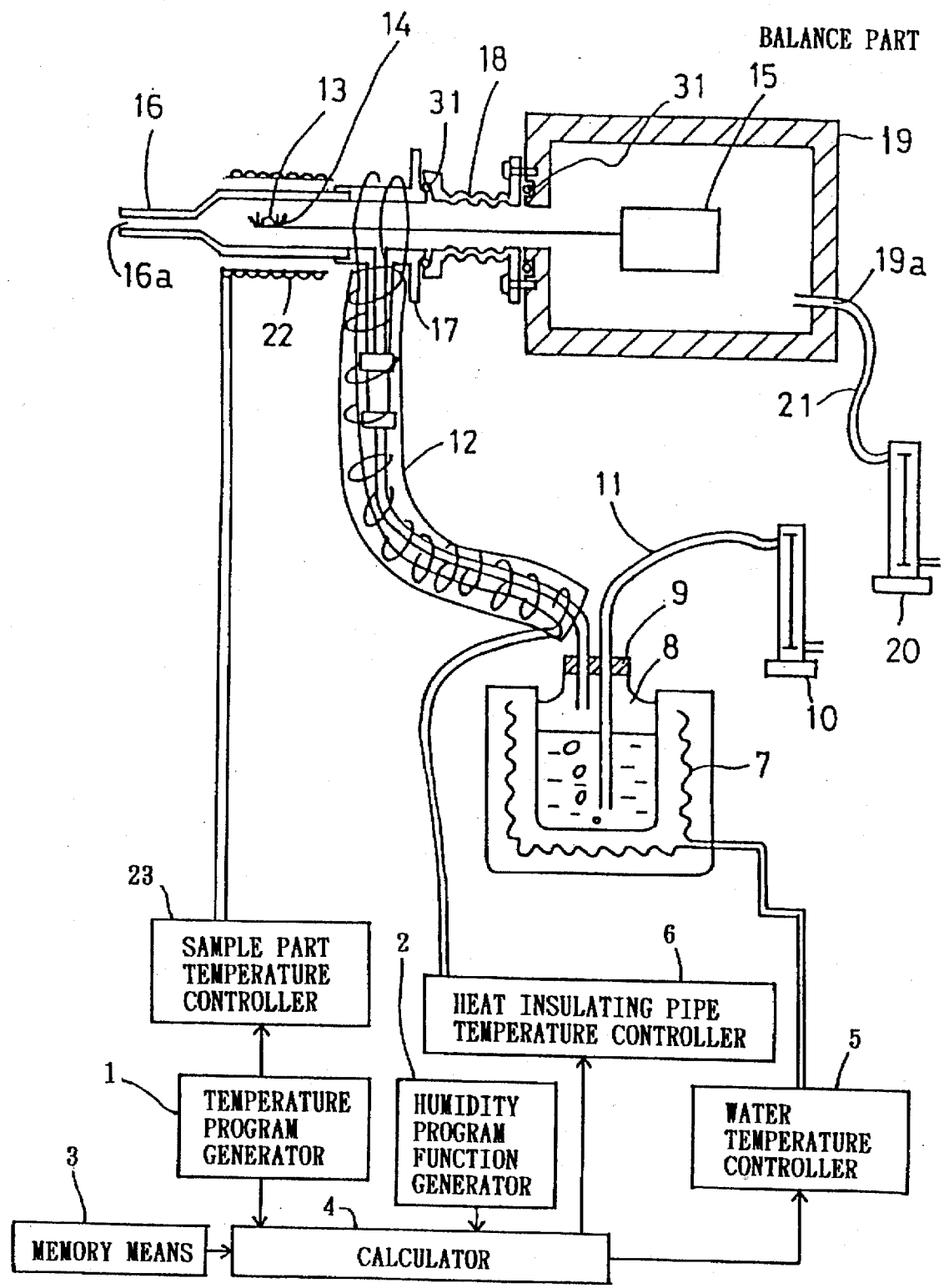
FIG. 1 is a schematic sectional view showing a thermal analyzer for performing thermal gravimetry (TG).

Embodiments of the present invention will be described in detail hereinbelow. FIG. 1 shows an embodiment of the invention in the form of an analyzer for performing thermal gravimetry (TG). This apparatus includes a temperature program function generator 1 into which an operator can input a predetermined temperature program and a humidity program function generator 2 into which the operator can input a desired humidity program. To the temperature program generator 1, a temperature controller 23 for the sample region is connected so that a sample temperature control heater 22 is controlled by temperature controller 23 on the basis of a known PID control. Then, the temperature of a sample 13 in the sample region changes in accordance with the temperature program for the sample 13.

The function relations $P=f(T)$ between the temperature $T(°C.)$ and the saturated water vapor pressure (mmHg) and the inverse function thereof $T=f^{-1}(P)$ can be stored in the form of polynomials in a memory means 3. The temperature program function generator 1, the humidity program generator 2 and the memory means 3 are all connected to a calculator 4. In the calculator 4, temperature values corresponding to the temperature program and the humidity program are calculated and are sent to a water temperature controller 5 and to a heat insulating pipe temperature controller 6.

The water temperature controller 5 is connected to a water temperature control heater 7. The temperature of water filling about 70% of a glass bottle 8 is PID controlled in accordance with the temperature values calculated by, and outputted from, the calculator 4. Further, the heat insulating pipe temperature controller 6 is connected to a heater embedded in a heat insulating pipe 12 so that the temperature within the heat insulating pipe 12 is controlled in accordance with the temperature values calculated by, and outputted from, the calculator 4, thereby preventing the dew condensation of water vapor inside the heat insulating pipe 12.

The glass bottle 8 is filled to about 70% with distilled water. The glass bottle 8 is sealed with a rubber cork, or cap, 9 which is penetrated by a bubbling gas introducing pipe 11 and a Teflon® tube which constitutes the core of the heat insulating pipe 12. One end of the bubbling gas introducing pipe 11 is connected to a source of an appropriate bubbling gas via a first flow meter 10 while the other end thereof is constantly immersed beneath the water surface inasmuch as that end is located in the vicinity of the bottom of the glass bottle 8. At the same time, with regard to the Teflon® tube which constitutes the core of the heat insulating tube 12, the end thereof that is housed in bottle 8 is located above the water surface in the glass bottle 8. The other end of the tube is connected to a stainless steel connecting pipe 17 via a stainless steel straight union. Further, a heater provided with an insulating coating is wound around each part, such as the Teflon® tube, the straight union, and the connecting pipe. Further, at least the Teflon® tube and the straight union is coated with heat insulating material to form heat insulating tube 12.

Sample 13 is housed in a furnace tube 16 which is made of sintered alumina and has a cylindrical configuration with a small diameter axial end forming a tip provided with a gas outlet 16a. The furnace tube 16 is connected to and fixed to connecting pipe 17 which has a water vapor inlet on one side. Further, a stainless-steel tube-like bellows 18 has one end secured to the connecting pipe 17 and its other end secured with the aid of screws to a balance case 19. Each end of bellows 18 is secured to pipe 17 or case 19, respectively, in a sealed manner with the aid of a respective O-ring 31.

A sample vessel containing the sample 13 is placed on a sample holder 14, and the weight change and temperature of the sample 13 are detected by means of a balance part 15 provided inside of the balance case 19 and mounted on a balance beam in which a thermocouple is installed.

The balance case 19 is provided with a purge gas inlet 19a for introducing a purge gas supplied by an appropriate gas source via a purge gas inlet pipe 21 and a second flow meter 20. A sample chamber is thus formed within the furnace tube 16, the connecting pipe 17 and the balance case 19.

The operation of the analyzer shown in FIG. 1 is as follows.

In the beginning, an operator separates sample temperature control heater 22, furnace tube 16 and connecting pipe 17 together from the tube-like bellows 18 and move them to the left. The sample holder 14 is then accessible for placement of a sample vessel containing the sample 13 thereon. Then, the sample temperature control heater 22, the furnace tube 16, and the connecting pipe 17 are reassembled to bellows 18 to be in the original configuration shown in FIG. 1.

A desired temperature program and a desired humidity program are input to the temperature program function generator 1 and the humidity program function generator 2, respectively. At this time, the humidity program can be input by selecting either relative humidity (%) units or water vapor pressure (mmHg) units. Further, the temperature program and the humidity program can be designated by setting target values for surface temperature and humidity of the sample 13 for each time interval as a function of time. Then, to protect the balance part 15 from moisture, a small amount (for example, 50 ml/min.) of dry air is allowed to flow via the flow meter 20 as the purge gas. Further, to send water vapor to the periphery of the sample 13, an appropriate amount (for example, 200 ml/min.) of dry air is allowed to flow through the flow meter 10 as the bubbling gas. The desired flow rate for the purge gas and the bubbling gas is input in the calculator 4.

When the measurement is started, the sample temperature control heater 22 is operated through sample part temperature controller 23 on the basis of the output to the temperature program function generator 1 so that the temperature of the sample 13 on the sample holder 14 is controlled within the furnace tube 16. In the meantime, in the calculator 4, the control target temperatures Tw (°C.) and Th (°C.) of the water temperature controller 5 and the heat insulating pipe controller 6, respectively, are calculated through the following calculations on the basis of the temperature output Tp (°C.) from the temperature program function generator 1, the output humidity Hp (mmHg or %) from the humidity program function generator 2, the function relations P=f(T) and T=f$^{-1}$(P) between the temperature T(°C.) output from the memory means 3 and the saturated water vapor pressure P (mmHg), and the flow rate Fp (ml/min.) of the purge gas and the flow rate Fb (ml/min.) of the bubbling gas.

a) When the temperature program is input in association with water vapor pressure (mmHg) units, the following mathematical equation are obtained.

$$Tw=f^{-1}[(1+Fp/Fb)\cdot Hp] \quad (1)$$

$$Th=Tw+20 \quad (2)$$

b) When the humidity program is input in association with relative humidity (%) units, the following mathematical expressions are obtained.

$$Tw=f^{-1}[(1+Fp/Fb)\cdot(Hp/100)\cdot f(Tp)] \quad (3)$$

$$Th=Tw+20 \quad (2)$$

Here, the function f$^{-1}$ represents an inverse function of the function f. In other words, the following relation is established.

$$f[f^{-1}(P)]=P \quad (4)$$

The aforementioned calculation results Tw (°C.) and Th (°C.) are sent from the calculator 4 to the water temperature controller 5 and the heat insulating pipe temperature controller 6, respectively, with the result that the distilled water in the glass bottle 8 and the region enclosed by heat insulating pipe 12 are controlled to have the temperatures Tw and Th, respectively. At this time, the dry air which is introduced into the water through the bubbling gas introducing pipe 11 becomes saturated with water vapor to an extent determined by the water temperature. Then, the moist air is sent to the region around the sample 13 via heat insulating pipe 12. At the periphery of the sample 13, the water vapor in the air is mixed with the purge gas sent via the flow meter 20 so that the level of the water vapor pressure is lowered in accordance with the ratio of dry air/purge gas flow rates. The water vapor introduced through the heat insulating pipe 12 is exhausted together with the purge gas from gas outlet 16a of the furnace tube 16. Since the temperature Th in the heat insulating pipe 12 is set to a value 20° C. higher than the water temperature Tw as shown in the mathematical expression (2), no dew condensation is formed inside of the heat insulating pipe 12.

In the meantime, when the temperature in the vicinity of the sample 13 is set to Tp and the water temperature is set to Tw, the water vapor pressure Ha (mmHg) and the relative humidity Hr(%) in the vicinity of the sample 13 are determined from the following mathematical equations:

$$Ha=f(Tw)\cdot Fb/(Fb+Fp) \quad (5)$$

$$Hr=100\cdot[(f(Tw)/f(Tp)]\cdot Fb/(Fb+Fp) \quad (6)$$

Here, the mathematical equations (1) and (3) are substituted in the right sides of the mathematical equations (5) and (6). Then, when the mathematical equations are put in order considering the condition of the mathematical expression (4), the relations Ha=Hp and Hr=Hp are obtained. Then, it becomes clear that the humidity around the sample is controlled in accordance with the humidity program value Hp input by the operator.

Figure 2:
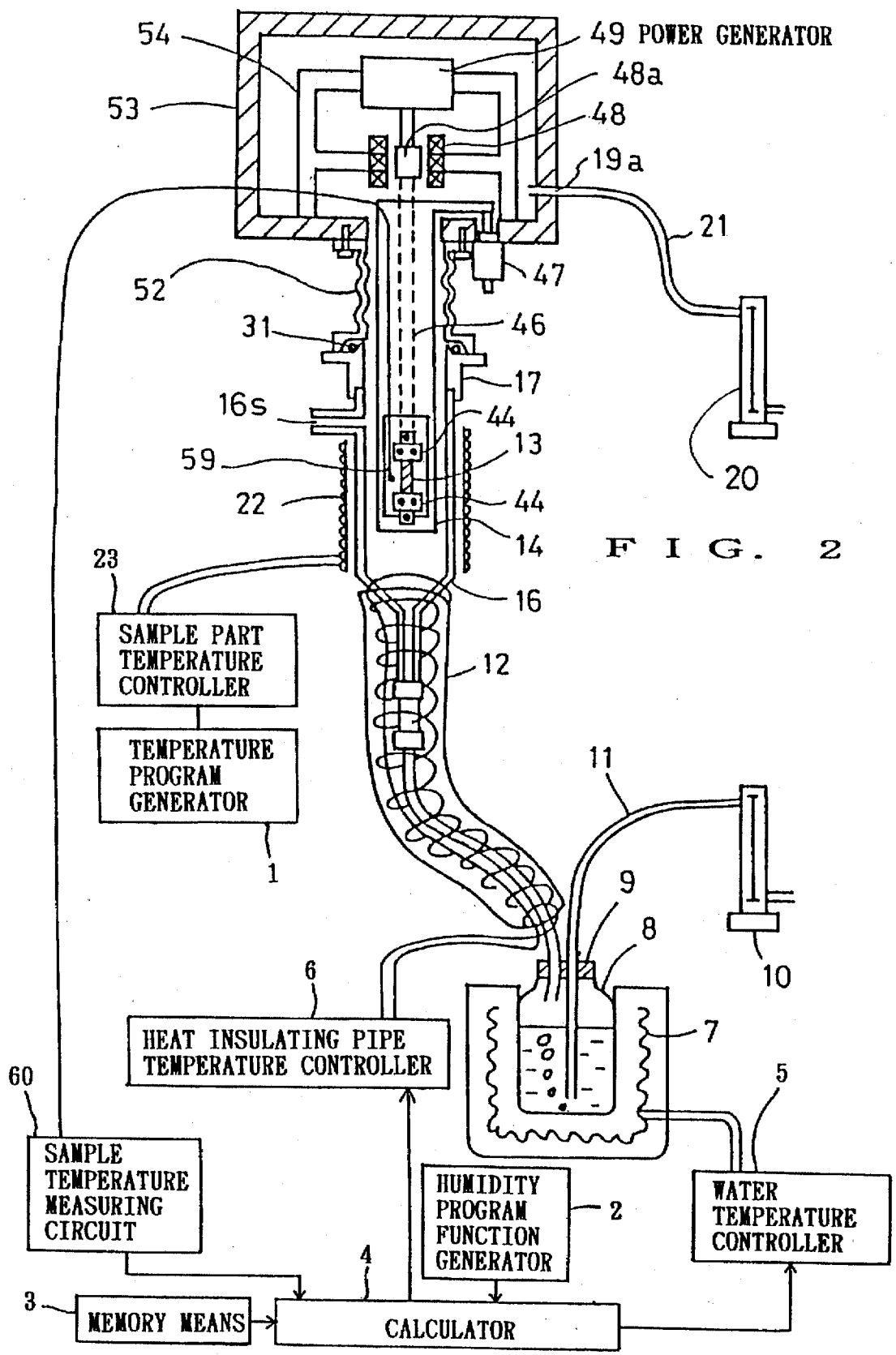
FIG. 2 is a schematic sectional view of the thermal analyzer for performing thermomechanical analysis (TMA).

FIG. 2 shows an analyzer according to the present invention applied to thermomechanical analysis (TMA). In FIG. 2, there are provided temperature program function generator 1 to which the operator can input a desired temperature program and humidity program function generator 2 to which the operator can input a desired humidity program. Sample part temperature controller 23 is connected to temperature program function generator 1 so that the sample temperature control heater 22 is controlled by the sample part temperature controller 23 on the basis of known PID control, and the temperature of a sample 13 changes in accordance with the temperature program. Further, the temperature of the sample 13 is directly detected with a thermocouple 59 arranged in the vicinity of the sample 13 and is measured with a sample temperature measuring circuit 60.

The function relation P=f(T) between the temperature T (°C.) and the saturated water vapor pressure P (mmHg) and the inverse function thereof T=f$^{-1}$(P) are stored in the form of polynomials in the memory means 3 in any case. The sample temperature measuring circuit 60, the humidity program function generator 2 and the memory means 3 are connected to calculator 4. In the calculator 4, temperature values corresponding to the temperature program and the humidity program are calculated and sent to water temperature controller 5 and the heat insulating pipe temperature controller 6. The water temperature controller 5 is connected to the water temperature control heater 7 so that the temperature of water filling about 70% of glass bottle 8 is PID controlled in accordance with the output temperature from the calculator 4. Further, the heat insulating pipe temperature controller 6 is connected to the heater embedded in heat insulating pipe 12, and the temperature within the heat insulating pipe 12 is controlled in accordance with the output temperature of the calculator 4, thereby preventing dew condensation of water vapor inside of the heat insulating pipe 12.

The distilled water fills about 70% of the glass bottle 8 and is sealed with rubber cork 9 which is penetrated by the bubbling gas introducing pipe 11 and the Teflon® tube which constitutes the core of the heat insulating pipe 12. One end of the bubbling gas introducing pipe 11 is connected to a source of bubbling gas via the flow meter 10 while the other end thereof is constantly immersed below the water surface since it is located in the vicinity of the bottom of the glass bottle 8. In the meantime, one end of the Teflon® tube which constitutes the core of the heat insulating pipe 12 is arranged above the water surface in the glass bottle 8 while the other end is connected to the end of the quartz glass furnace tube 16 via a stainless steel straight union. In the meantime, the heater coated with an insulator is wound around each part at the end of the Teflon® tube, the straight union, and a part of the furnace tube, and is coated with heat-resistant heat insulating material thereby forming the heat insulating pipe 12.

Tube 16 is here made of quartz glass, has a cylindrical configuration, has one end connected to the heat insulating pipe 12, and has a gas outlet 16s at its side surface at the upper end thereof. The upper end of furnace tube 16 is connected and fixed to a connecting pipe 17 formed of stainless steel and having a cylindrical configuration. An O-ring 31 is interposed between bellows 52 and pipe 17 to form a seal therebetween. Further, a stainless steel tube-like bellows 52 is fixed to a detector case 53 by means of fastening screws. Each end of the sample 13 is gripped with a respective inconel chuck 44. Each chuck 44 is fixed with screws to a respective one of a stainless steel detecting rod 46 and a stainless steel sample holder 14. The upper and lower positions of the sample holder 14 can be adjusted to the length of the sample 13 with a micrometer 47 fixed to the detector case 53.

A pulling force is transmitted to the sample 13 from power generator 49 connected to the upper end of the detecting rod 46. Changes in the length of the sample 43 are transmitted to a differential transformer core 48a fixed to the upper part of the detecting rod 46 as a movement of the detecting rod 46 so that the change is detected as a change in a relative position between the sample 13 and a differential transformer coil 48 fixed via a holding member 54 to the detector case 53.

Further, the temperature of the sample 13 is simultaneously detected with the aid of thermocouple 60 arranged in the vicinity of the sample 13. Consequently, when the force applied to the sample by the power generator 49 is either statically, or alternatively dynamically, set with the aforementioned structure, physical values such as the viscoelasticity of the sample, stress and distortion can be determined from the change in the length of sample and relations between changes in length and force, which relations are already well known in the art.

On part of the detector case 53, a purge gas inlet 19a is provided for introducing a purge gas via the purge gas introducing pipe 21. A sample chamber is formed by the interior of case 53, the furnace tube 16 and the connecting pipe 17.

The operation of the analyzer shown in FIG. 2 is as follows. In the beginning, the operator disconnects the sample temperature control heater 22, the furnace tube 16 and the connecting pipe 17 together from the tube-like bellows 52 and moves them downwardly. In the state in which the end of the sample holder 14 is exposed, respective ends of the sample 13 are fixed to the detecting rod 46 and the sample holder 14 by means of screws and chucks 44. Then, the sample temperature control heater 22, the furnace tube 16, and the connecting pipe 17 are brought back to the original position and pipe 17 is reconnected to bellows 52.

A desired temperature program and a desired humidity program are input to the temperature program function generator 1 and the humidity program function generator 2, respectively. At this time, the humidity program can be input by selecting either relative humidity (%) units or water vapor pressure (mmHg) units. Further, the temperature program and the humidity program are designated by setting the target values of the temperature and humidity at the periphery of the sample 13 for each time period, or increment, as time functions.

Then, to protect the inside of the detector case 53 from the humidity, an appropriate amount (for example, 500 ml/min.) of dry air is allowed to flow as a purge gas through the flow meter 20. Further, to contact the periphery of the sample 13 with an atmosphere containing water vapor, an appropriate amount (for example, 500 ml/min.) of dry air is allowed to flow as a bubbling gas through the flow meter 10.

When the measurement is started, the sample temperature control heater 22 is operated through the sample part temperature controller 23 on the basis of the output of the temperature program function generator 1 so that the temperature of the sample 13 in the sample holder 14 is controlled through the furnace tube 16. In the meantime, in the calculator 4, the control target temperatures Tw (°C.) and Th (°C.) of the water temperature controller 5 and the heat insulating pipe controller 6, respectively, are calculated by the following calculations on the basis of the temperature output Ts (°C.) from the sample temperature measuring circuit 60, the output humidity Hp (mmHg or %) from the humidity program function generator 2, the function relations P=f(T) and T=f$^{-1}$(P) between the temperature T (°C.) output from the memory means 3 and the saturated water vapor pressure P (mmHg).

a) When the humidity program is input in water vapor pressure (mmHg) units, the following mathematical equations are obtained.

$$Tw=f^{-1}(Hp) \tag{7}$$

$$Th=Tw+20 \tag{2}$$

b) When the humidity program is input in relative humidity (%) units, the following mathematical equations are obtained.

$$Tw=f^{-1}[(Hp/100) \cdot f(Ts)] \tag{8}$$

$$Th=Tw+20 \tag{2}$$

Here, the function f$^{-1}$ represents the inverse function of function f.

The aforementioned calculation results Tw (°C.) and Th (°C.) are sent from the calculator 4 to the water temperature controller 5 and the heat insulating pipe temperature controller 6 with the result that the distilled water in the glass bottle 8 and the heat insulating pipe 12 are controlled in temperature to Tw and Th, respectively. At this time, the dry air which is introduced into the water through the bubbling gas introducing pipe 11 is converted into saturated water vapor based on the water temperature. Then the air containing water vapor flows to the periphery of the sample 13 via heat insulating pipe 12, and then is exhausted together with the purge gas from the gas outlet 16s of the furnace tube 16. Since the temperature Th of the heat insulating pipe 12 is set to a value 20° C. higher than the water temperature Tw, as shown in the mathematical expression (2), no dew condensation is formed inside of the heat insulating pipe 12.

In the meantime, when the temperature in the vicinity of the sample 13 is set to Ts and the water temperature is set to Tw, a water vapor pressure Ha (mmHg) and a relative humidity Hr (%) in the vicinity of the sample 13 are determined as follows. That is, the following equations are obtained.

$$Ha=f(Tw) \quad (9)$$

$$Hr=100 \cdot (f(Tw))/f(Ts)) \quad (10)$$

Here, the equations (7) and (8) are substituted in the right side of the mathematical expressions (9) and (10). Then, when the equations are put in order considering the condition of the equation (4), relations Ha=Hp and Hr=Hp are obtained. Then, it becomes clear that the temperature around the sample is controlled in accordance with the humidity program value Hp input by the operator.

In this embodiment, an explanation has been given with respect to the measurement of tensile characteristics of the sample. It is known that the measurement of compression, bending and shearing or the like can be easily conducted when the structure to which the sample is connected is changed.

Incidentally, in the embodiments shown in FIGS. 1 and 2, an explanation is given with respect to a case in which the temperature of the heat insulating pipe is set 20° C. higher than the water temperature. It goes without saying that the temperature could be set to other temperature ranges. In such a case, 20 in the equation (2) may be changed to other values. Further, in the embodiments shown in FIGS. 1 and 2, the water temperature is controlled by using the water temperature heater. However, a similar function can be realized by using a circulation basin provided with a temperature control system. Further, the function relation between the temperature and the saturated vapor pressure can use approximate expressions such as exponents and logarithms in addition to polynomial approximations. Further, it goes without saying that an appropriate humidity sensor can be arranged in the vicinity of the sample if needed to accurately monitor the humidity around the samples. In the meantime, it is possible to provide a valve in the bubbling gas introducing pipe and an ON/OFF switch for the introduction of the water vapor can be provided so as to be able to control the switching from the outside.

In accordance with the present invention, changes in the physical characteristics of a sample can be measured by automatically controlling the temperature and humidity of the sample in accordance with the program designated by the operator in advance. Consequently, it is possible to accurately judge by selecting the program conditions whether the observed change is a phenomenon which depends on the temperature, or depends on the humidity. Further, the measurement can be easily carried out for varying the temperature at a constant rate while keeping the relative humidity at a constant level despite the fact that such measurement was conventionally difficult. Further, in accordance with the present invention, since it is possible to add a new function as a humidity dependency evaluation means which can be handled with the same ease as the conventional thermal analysis method that has been useful as a temperature dependency evaluation means of the change in the physical characteristics, a universal-purpose analysis evaluation method can be obtained to aid the development of improved materials.

Figure 3:
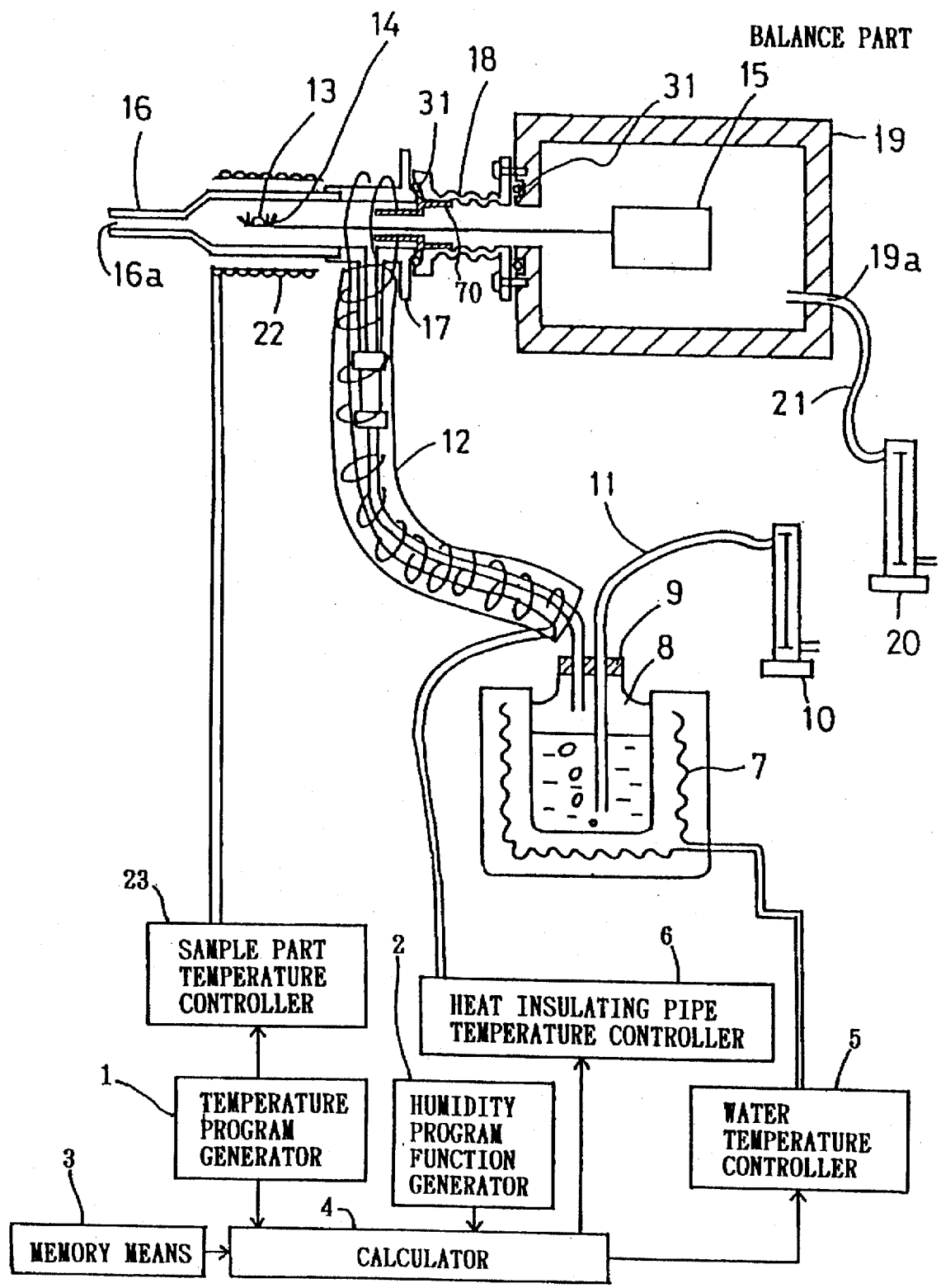
FIG. 3 is a view similar to that of FIG. 1 showing a modified version of the thermal analyzer of FIG. 1.

FIG. 3 shows another embodiment which closely resembles the embodiment shown in FIG. 1. The sample chamber is formed with the furnace tube 16 and the connecting pipe 17. In this embodiment, a steam inlet portion is provided with the connecting pipe 17 for introducing steam into the sample chamber. An outlet 16a is formed at the opposite end of the furnace tube 16 remote from the connecting pipe 17 side. The steam inlet portion is attached with the heat insulating tube 12 as described before. The connecting pipe 17 is attached to the case 19 in which detecting means is provided, through the tube-like bellows 18. An inner pipe 70 is arranged between the steam inlet portion and the case 19 at the inside of the bellows 18 and the connecting pipe 17. The inner pipe 70 is kept warm by heat transfer through the bellows 18 and the connecting pipe 17 from the heat insulating tube and then dew condensation does not occur on the surface of the inner pipe 70. The outside of the inner pipe 70 is substantially kept air tight by the inside of bellows 18 and the connecting pipe 17. The inner pipe 70 provides a through hole centered on its longitudinal axis for introducing movably the transfer means for transferring the change of the physical value of the sample depending on temperature. The inside dimension of the inner pipe 70 at the end facing the case 19 is bigger than that of the end facing away from the case 19. The inner pipe 70 is provided for preventing a reverse flow of the steam (water vapor) from the sample chamber to the inside of the case 19. The purge gas always flows from the inside of the case 19 to the gas outlet 16a in operation. Therefore, the device in the case 19 is isolated from the steam.

This application relates to subject matter disclosed in Japanese Application number 6-286961, filed on Nov. 21, 1994, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A humidity control thermal analyzer comprising:
    a detector for detecting and measuring a physical characteristic of a sample;
    a sample chamber for housing the sample and which is provided with a vapor inlet and a vapor outlet for water vapor and which is capable of controlling the temperature of the sample housed in said sample chamber;
    a heat insulating pipe with heating means for preventing dew condensation, said pipe being connected to said vapor inlet of said sample chamber;
    a warm water container for generating water vapor, said container having a gas inlet and having a gas outlet which is connected to said pipe and which is capable of controlling the temperature of water in said container;
    a temperature program function generator for outputting a target temperature value of said sample chamber as a function of time;
    a humidity program function generator for outputting a target humidity value of said sample chamber as a function of time;
    a memory means for storing a temperature-saturated water vapor pressure curve; and a calculator connected to said function generators and said memory means for calculating a control target temperature for the water in said container for generating a saturated water vapor pressure on the basis of the sample chamber target temperature output from the temperature program function generator, the sample chamber target humidity value of the sample chamber output from the humidity program function generator and the temperature-saturated water vapor pressure curve, wherein the temperature of the sample and the humidity of the atmosphere contacting the sample are program controlled.

2. A humidity control thermal analyzer according to claim 1 wherein the physical characteristics of the sample detected by said detector include the weight of the sample.

3. A humidity control thermal analyzer according to claim 1 wherein the sample has a length and the physical characteristics of the sample detected by said detector include the length of the sample.

4. A humidity control thermal analyzer according to claim 1 wherein the physical characteristics of the sample detected by said detector include one of viscoelasticity, stress and distortion of the sample.

5. A humidity control thermal analyzer according to claim 1 wherein the temperature of said heat insulating pipe is controlled to a target temperature associated with the temperature of the warm water container for generating saturated water vapor pressure.

6. A humidity control thermal analyzer according to claim 1 wherein a said temperature-saturated water vapor pressure curve is stored in said memory means as a function based on an approximate equation.

7. A humidity control thermal analyzer according to claim 1 wherein said humidity program function generator contains a program based on one of relative humidity units and water vapor pressure units.

8. A humidity control thermal analyzer according to claim 1, wherein:

said sample chamber has a sample holding location for holding the sample;

said sample chamber further comprises a case enclosing said detector, said case having a purge gas inlet for receiving a purge gas and said case being spaced from said sample location;

said vapor inlet of said sample chamber is located between said sample location and said case and said vapor outlet is located at an end of said sample chamber remote from said case;

said analyzer further comprises an inner pipe provided inside of the sample chamber between said case and vapor inlet; wherein flow of water vapor into said case is prevented by a flow of purge gas through said purge gas inlet.

9. A humidity control thermal analyzer comprising:

a detector for detecting and measuring a physical characteristic of a sample;

a sample chamber for housing the sample and which is provided with a vapor inlet and a vapor outlet for water vapor and which is capable of controlling the temperature of the sample housed in said sample chamber;

a sample temperature detector which is disposed in said sample chamber for detecting the temperature of the sample;

a heat insulating pipe with heating means for preventing dew condensation, said pipe being connected to said vapor inlet of said sample chamber;

a warm water container for generating water vapor, said container having a gas inlet and having a gas outlet which is connected to said pipe and which is capable of controlling the temperature of water in said container;

a temperature program function generator for outputting a target temperature value of said sample chamber as a function of time;

a humidity program function generator for outputting a target humidity value of said sample chamber as a function of time;

a memory means for storing a temperature-saturated water vapor pressure curve; and a calculator connected to said sample temperature detector, said humidity program function generator and said memory means for calculating a control target temperature for the water in said container for generating a saturated water vapor pressure on the basis of the sample temperature detected by said sample temperature detector, the sample chamber target humidity value of the sample chamber output from the humidity program function generator and the temperature-saturated water vapor pressure curve, wherein the temperature of the sample and the humidity of the atmosphere contacting the sample are program controlled.

10. A humidity control thermal analyzer according to claim 9 wherein the physical characteristics of the sample detected by said detector include the weight of the sample.

11. A humidity control thermal analyzer according to claim 9 wherein the sample has a length and the physical characteristics of the sample detected by said detector include the length of the sample.

12. A humidity control thermal analyzer according to claim 9 wherein the physical characteristics of the sample detected by said detector include one of viscoelasticity, stress and distortion of the sample.

13. A humidity control thermal analyzer according to claim 9 wherein the temperature of said heat insulating pipe is controlled to a target temperature associated with the temperature of the warm water container for generating saturated water vapor pressure.

14. A humidity control thermal analyzer according to claim 9 wherein a said temperature-saturated water vapor pressure curve is stored in said memory means as a function based on an approximate equation.

15. A humidity control thermal analyzer according to claim 9 wherein said humidity program function generator contains a program based on one of relative humidity units and water vapor pressure units.

* * * * *